United States Patent [19]

Ohama

[11] Patent Number: 4,460,143
[45] Date of Patent: Jul. 17, 1984

[54] VIAL SUSPENDER

[75] Inventor: Tadahiro Ohama, Kyoto, Japan

[73] Assignee: Fujisawa Pharmaceutical Co., Ltd., Osaka, Japan

[21] Appl. No.: 331,180

[22] Filed: Dec. 16, 1981

[30] Foreign Application Priority Data

Apr. 23, 1981 [JP] Japan .................. 56-59467[U]
Jun. 23, 1981 [JP] Japan .................. 27590
Sep. 14, 1981 [JP] Japan .................. 56-137206[U]

[51] Int. Cl.$^3$ .................................. A47B 91/00
[52] U.S. Cl. ............................ 248/359; 215/100 A
[58] Field of Search ........... 248/359, 360, 318, 317, 248/311.3; 215/100 A, 100 R, 13 R

[56] References Cited

U.S. PATENT DOCUMENTS

| | | | |
|---|---|---|---|
| 2,304,547 | 12/1942 | Cutter | 248/359 |
| 2,635,604 | 4/1953 | Fredrickson | 215/100 A X |
| 3,387,732 | 6/1968 | Jellies | 215/100 A |
| 3,425,653 | 2/1969 | Rauch | 248/318 X |
| 3,635,367 | 1/1972 | Morita | 248/359 X |
| 3,901,399 | 8/1975 | McPhee | 215/100 A |
| 4,093,169 | 6/1978 | Winchell | 215/100 A X |
| 4,306,662 | 12/1981 | Sciortino | 248/359 X |

Primary Examiner—J. Franklin Foss
Attorney, Agent, or Firm—Jordan B. Bierman; Linda Bierman

[57] ABSTRACT

A vial suspender comprising a planar base plate and a suspending portion including a suspending strip and a suspending ring and joined to the center of the base plate by a hinge portion. The suspending portion is foldable at another hinge portion and is accommodated in a folded position in recesses formed in the base plate. The base plate is fastened to the bottom of a vial with a heat-shrunken resin film. When pulled out from the base plate to an unfolded position, the suspending portion has a sufficient length to support the vial in a substantially vertical, inverted position.

4 Claims, 4 Drawing Figures

VIAL SUSPENDER

The present invention relates to a vial suspender, and more particularly to a device for suspending vials containing pharmaceutical parenteral solutions, nutrient solutions, etc. for dropwise administration.

Such suspenders of various types have been developed, but they have the drawback of being inconvenient to use, for example, because the suspending portion is short or because the suspending portion is biased strongly toward the bottom of the vial.

The object of the present invention is to overcome the above problem and to provide a suspender comprising a suspending portion which has hinge portions and which is thereby adapted to have a sufficient length and rendered positionable at any desired angle with respect to the bottom of a vial without being biased toward the bottom of the vial.

The present invention will be described below with reference to the accompanying drawings, in which.

Figure 1:
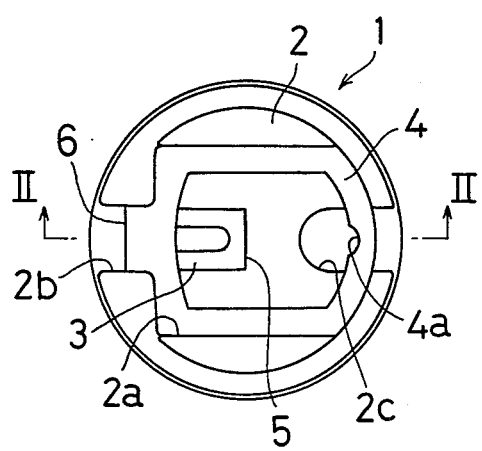
FIG. 1 is a plan view showing a vial suspender embodying the invention.
Figure 2:
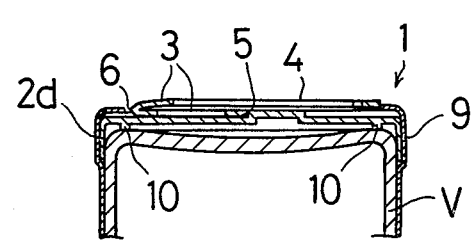
FIG. 2 is a fragmentary view in vertical section taken along the line II—II in FIG. 1 and showing the suspender as fastened to the bottom of a vial.

With reference to FIGS. 1 and 2, a vial suspender 1 of this invention is fastened to the bottom of a vial V. The vial suspender 1 is made of polypropylene and includes a base plate 2, a suspending strip 3 and a suspending ring 4 which are molded integrally. One end of the suspending strip 3 is joined by a hinge portion 5 of reduced thickness to the center of the planar base plate 2. The other end of the suspending strip 3 is continuous with the suspending ring 4. The suspending strip 3 has a hinge portion 6 of reduced thickness. When the suspending portion comprising the strip 3 and the ring 4 is folded at the hinge portion 6 as shown in FIG. 1, the distance from the center of the planar base plate 2 to the free end of the suspending ring 4 is approximately equal to the distance from the center to the hinge portion 6. The base plate 2 has a recess 2a for accommodating the suspending ring 4 therein. The bottom of the recess 2a further has a recess 2b for accommodating the base portion of the suspending strip 3 therein.

The suspending ring 4 is formed with two projections 7, 7 arranged symmetrically on one side of its base portion to be opposed to the base plate 2 when the suspending portion is folded and accommodated in the base plate 2. The base plate 2 has bores 8, 8 in corresponding relation to the projections 7, 7. These projections 7, 7 are engageable in the bores 8, 8 respectively.

The base plate 2 has a cavity 2c at one side thereof to be opposed to the free end of the suspending ring 4 when the suspending portion is accommodated in the base plate 2 in its folded position, i.e. at the side thereof opposite to the recess 2b. With the cavity 2c thus formed, the suspending portion can be easily pulled out from the base plate 2 to a raised position. The peripheral portion of the base plate 2 is flush with the bottom surface of the recess 2a except at the recess 2b and the cavity 2c. A heat-shrinkable resin film 9 covering this peripheral portion and the bottom side wall portion of the vial V is thermally shrunken to fasten the suspender 1 to the bottom of the vial V. A side wall 2d extends from the outer periphery of the base plate 2 to hold the suspender 1 in engagement with the bottom of the vial V effectively. An annular projection 10 is formed on the bottom surface of the base plate 2 inwardly of the side wall 2d to assure this engagement. When the bottom surface of the base plate 2 is planar, however, the annular projection 10 can be dispensed with without impairing the engagement between the suspender and the vial. The suspending ring 4 has a cutout 4a on the inner side of its free end to render the vial suspendable with improved stability.

Before use, the suspender is fastened to the bottom of the vial, with the suspending strip 3 and the suspending ring 4 accommodated in the recesses 2b and 2a of the base plate 2 respectively and also with the projections 7, 7 engaged in the bores 8, 8. When the vial is to be used, the suspending strip 3 and the suspending ring 4 are pulled out from the base plate 2 to an unfolded position as seen in FIG. 3, and the suspender is hung on a hanger H as shown in FIG. 4.

Figure 3:
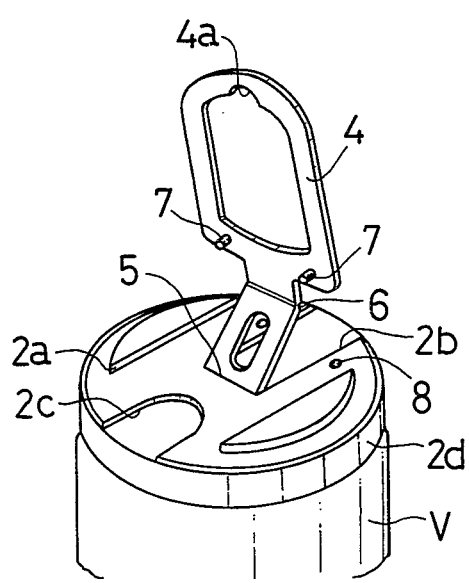
FIG. 3 is a fragmentary perspective view showing the same with its suspending portion in a pulled-up position.
Figure 4:
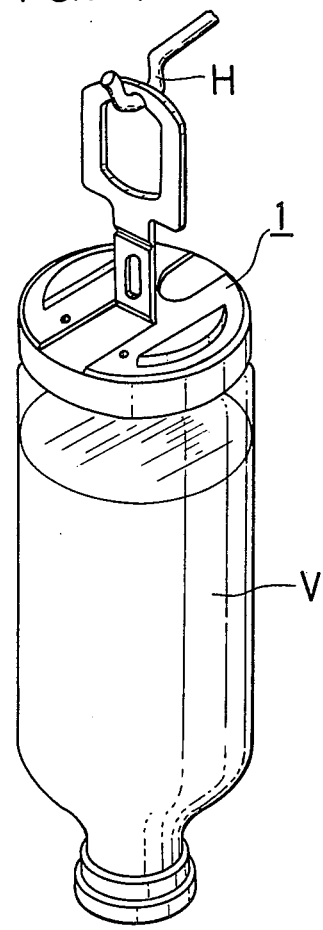
FIG. 4 is a perspective view showing the suspender in use.

It will be seen also from these FIGS. 3 and 4 that the suspending portion including the suspending strip 3 and the suspending ring 4 has a sufficient length and that the suspending portion pulled out from the base plate 2 to its unfolded position can be held in an upright position approximately perpendicular to the base plate 2. Accordingly the user can easily hang the vial V on the hanger H which is at a level higher than his height, by gripping the neck of the vial V instead of holding the upper end of the suspender 1 in the conventional manner. The suspender 1 of this invention is therefore convenient to use.

Because the suspending strip 3, unlike the suspenders of this type heretofore known, is not strongly biased toward the base plate 2 and further because the base portion of the strip 3 is located at the center of the planar base plate 2, the vial V can be suspended in a vertical inverted position.

Additionally when a plurality of vials are suspended from a single hanger, the sufficient length of the suspending portion stated above will not permit each vial to be positioned in an inclined position owing to contact with another vial at the bottom portion. Thus the present suspender assures improved safety.

While the suspending portion is accommodated in place in its folded position, the projections 7 fitting in the bores 8 firmly hold the suspending portion in engagement with the base plate 2, thereby eliminating the likelihood that the suspending portion will be inadvertently released from the base plate 2 before use. The present suspender is further convenient in that the suspending portion can be easily pulled out for use by inserting the nail into the cavity 2c.

FIGS. 1 to 4 show an embodiment of the invention for illustrative purposes only. Provided that the contemplated object can be fulfilled, the vial suspender described above can be modified as desired in respect of the material and shape of the suspender, the location and number of hinge portions formed in the suspending portion, the means for attaching the suspender to the bottom of the vial, etc.

The projections and the bores for holding the suspending portion folded in engagement with the base plate can be located as desired insofar as they serve the contemplated purpose. For example, the projections may be provided on the base plate, and the bores in the suspending portion. The bores need not always extend through the base plate or the suspending portion but may have a bottom.

Further when a heat-shrinkable resin film is used for fastening the suspender to the bottom of the vial as in the foregoing embodiment, the resin film as well as the suspender may be made to have light blocking properties, in which case the suspender is advantageously usable for pharmaceutical preparations having low stability to withstand light.

As will be apparent from the above description, the vial suspender of this invention is simple in construction, inexpensive to make, convenient to use and therefore very useful.

What is claimed is:

1. A vial suspender comprising a planar baseplate formed of plastic material and adapted on its underside to be attached to a vial bottom and a suspending portion formed integrally with said baseplate of the same plastic material and adapted to extend from the opposite side of said baseplate, said suspending portion comprising a first foldable portion notch-hinged at one end to said baseplate and a suspending strip formed as an integral continuation of said first foldable portion notch-hinged at one end to the other end of said first foldable portion, whereby said suspending portion may be folded substantially flat against said vial bottom but when extended, both said first foldable portion and said sustaining strip extend upwardly from said baseplate at a substantially 90° C. angle.

2. A vial suspender according to claim 1, in which said baseplate is formed with a cutout section adapted to receive said first foldable portion so that the latter may lie substantially coplanar with the opposite side of said baseplate.

3. A vial suspender according to claim 2, in which said baseplate is formed with a pair of openings on its upper surface and in which said sustaining strip is formed with a pair of integral depending pins adapted to form a force fit into said openings when said suspending portion lies flat against the vial bottom.

4. A vial suspender according to claim 1 wherein said underside further comprises a skirt of a heat-shrinkable resin attached thereto for thermal shrinkage around a vial.

* * * * *